(12) United States Patent
Roberts

(10) Patent No.: US 10,722,412 B2
(45) Date of Patent: Jul. 28, 2020

(54) COLLAPSIBLE INCUBATOR

(71) Applicant: MOM Incubators Ltd, Kent (GB)

(72) Inventor: James Michael Roberts, Surrey (GB)

(73) Assignee: MOM Incubators Ltd, Kent (GB)

( * ) Notice: Subject to any disclaimer, the term of this patent is extended or adjusted under 35 U.S.C. 154(b) by 76 days.

(21) Appl. No.: 15/317,799

(22) PCT Filed: Jun. 11, 2015

(86) PCT No.: PCT/GB2015/000169
§ 371 (c)(1),
(2) Date: Dec. 9, 2016

(87) PCT Pub. No.: WO2015/189541
PCT Pub. Date: Dec. 17, 2015

(65) Prior Publication Data
US 2017/0119609 A1    May 4, 2017

(30) Foreign Application Priority Data

Jun. 11, 2014 (GB) .................................. 1410442.6
Nov. 6, 2014 (GB) .................................. 1419800.6

(51) Int. Cl.
*A61G 11/00* (2006.01)
*A61M 16/16* (2006.01)
(Continued)

(52) U.S. Cl.
CPC ............ *A61G 11/005* (2013.01); *A61B 90/30* (2016.02); *A61F 7/10* (2013.01); *A61G 11/00* (2013.01);
(Continued)

(58) Field of Classification Search
CPC ...... A61G 11/00–009; A61G 10/00–04; A62B 31/00; A62B 1/00
(Continued)

(56) References Cited

U.S. PATENT DOCUMENTS 2,600,501 A * 6/1952 Higgs .................... A62B 31/00
600/22
2,915,074 A    12/1959 Cameto
(Continued)

FOREIGN PATENT DOCUMENTS

DE    20 2008 006630 U1    9/2008
FR    1 533 307 A    7/1968
(Continued)

OTHER PUBLICATIONS

PCT International Search Report from International Application No. PCT/GB2015/000169, dated Oct. 8, 2015, 10 pages.
(Continued)

*Primary Examiner* — Catherine B Kuhlman
(74) *Attorney, Agent, or Firm* — Tucker Ellis LLP; Michael G. Craig

(57) ABSTRACT

A collapsible incubator for an infant, the collapsible incubator comprising: a flexible housing for containing the infant, the flexible housing being configurable between an expanded condition and a collapsed condition; a door within the flexible housing for infant access; a first end portion secured to a first end of the flexible housing; a second end portion secured to a second end of the flexible housing, said second end portion being configured to be substantially opposite said first end portion; and, at least one fastening means configured to releasably secure the first end portion to the second end portion when in the collapsed condition, whereby the first end portion and the second end portion are configured, in use, to support the flexible housing in the expanded condition, and to substantially contain the flexible housing therebetween in the collapsed condition.

17 Claims, 6 Drawing Sheets

(51) Int. Cl.
  *A61B 90/30* (2016.01)
  *A61F 7/10* (2006.01)
  *A61M 16/20* (2006.01)
  *A61B 17/00* (2006.01)
(52) U.S. Cl.
  CPC .......... *A61G 11/003* (2013.01); *A61G 11/009* (2013.01); *A61M 16/16* (2013.01); *A61M 16/20* (2013.01); *A61B 2017/00991* (2013.01); *A61G 2203/30* (2013.01)
(58) Field of Classification Search
  USPC .......................................................... 600/22
  See application file for complete search history.

(56) References Cited

U.S. PATENT DOCUMENTS

| | | | |
|---|---|---|---|
| 3,818,896 A | | 6/1974 | Deaton |
| 3,877,427 A | | 4/1975 | Alexeev et al. |
| 5,498,229 A | * | 3/1996 | Barsky .................. A61G 11/00 600/122 |
| 6,500,111 B1 | * | 12/2002 | Salmon ................ A61G 10/005 600/22 |
| 9,980,869 B2 | * | 5/2018 | Lehmann ............ A61M 16/161 |
| 2008/0319249 A1 | * | 12/2008 | Kuo ...................... A61F 7/0053 600/22 |
| 2015/0126804 A1 | * | 5/2015 | Rapoport ................ A61G 10/00 600/22 |
| 2015/0209598 A1 | * | 7/2015 | Bhosale ................. A61N 5/0621 607/90 |

FOREIGN PATENT DOCUMENTS

| | | | |
|---|---|---|---|
| GB | 2 137 504 A | | 10/1984 |
| GB | 2137504 A | * | 10/1984 ............ A61G 11/00 |
| WO | WO-9748363 A1 | * | 12/1997 ............ A47D 13/02 |
| WO | 2008/014617 A1 | | 2/2008 |
| WO | 2014/159951 A1 | | 10/2014 |
| WO | 2014/189874 A1 | | 11/2014 |

OTHER PUBLICATIONS

GB Search and Exam Report from GB1419800.6, dated Mar. 31, 2015, 6 pages.

* cited by examiner

COLLAPSIBLE INCUBATOR

BACKGROUND

This invention pertains generally to the field of collapsible incubators, and in particular collapsible incubators for neonatal use.

An incubator is an apparatus that is typically used to maintain various environmental conditions suitable for a neonate or newborn baby, and in particular those infants that are born prematurely or those that need additional support to survive. These infants battle to regulate their own body temperature and do not have sufficient fat stores on their body to stay warm.

However, whilst these neonatal incubators are readily available in hospitals throughout most of the Western world, they are cumbersome to transport for use in the field, and are an extremely expensive apparatus, making them unfeasible for use in developing countries.

There are various forms of incubation that an incubator may be required to perform to help support an infant to develop and grow in a safe environment for the best chance of survival. An incubator, in its most basic form, comprises a shell into which an infant can be placed, that protects the infant from their surrounding environment. This shell shields them from extremes of temperature, draughts and other environmental conditions, whilst minimising infection by limiting their exposure to germs, bacteria and infectious diseases. The shell prevents the ingress of dirt and other detritus that may affect their respiratory airways, whilst also preventing over-handling by carers and other personnel.

There are numerous additional functions that can be added to a basic incubator module to provide additional support to the infant contained therein. The infant may be supplemented with oxygen through an oxygen supply means or mechanical ventilation means. The apparatus might include measuring means for various vital signs such as heart beat, breathing rate, temperature and blood pressure and other measurable bodily functions such as brain activity, blood oxygen levels and cardiac performance. The incubator may include means to provide an effective climate control within the shell to keep the infant at the required temperature. The incubator may also be supplied with nutritional support means through an intravenous catheter or suchlike, to help with administering medications and to help the infant to remain hydrated.

Neonatal transport incubators provide a similar infant support apparatus when away from a hospital-type environment. They typically provide very similar functionality, just in a transportable form. For an example, a transport incubator might include a miniature ventilator, cardio-respiratory monitor, intravenous therapy pump, pulse oximeter and an oxygen supply means, or any combination of these.

However, whilst these transport incubators would be extremely sought after within the developing world and in disaster relief situations throughout the world, they are an extremely expensive item and the cost renders them unavailable in such areas. Access to incubators is limited by both cost and distance, and millions of premature and sick infants die each year through deaths that may have been prevented had they have had sufficient care. The apparatus that is currently available within these areas is not cheap enough, nor is it sufficiently portable.

The prior art shows a number of devices which attempt to address the needs in various ways.

GB 2,450,392 (Drager Medical AG) discloses an incubator with an inflatable and collapsible hood. The heat therapy apparatus comprises a bed area with an inflatable hood for covering the bed area, whereby the inflatable hood is provided with a plurality of inflatable, tubular support elements with interposed plastic sheets. The plastic sheet may be double-walled to provide insulation to the space contained within. The intention is to provide the structural features of an open care infant bed with the benefits of a closed incubator, by providing an inflatable hood to fit over a typically infant care bed. Whilst this document discloses an inflatable shell, which is therefore collapsible, the bed portion is not designed for this purpose. The resulting incubator is therefore not designed for portable use.

CN 201,591,700 (Lifang) discloses an inflatable bed for a premature infant. This inflatable bed is designed to create an artificial uterine cavity, provided with an inflatable cushion. This device is intended for use within existing incubators, and therefore is not a portable alternative to the incubator itself.

U.S. Pat. No. 3,818,896 (Medical Concepts Inc) discloses an inflatable housing to enclose a volume of atmosphere for use as an incubator or oxygen tent. This inflatable housing is intended to replace the rigid framework or housing of incubators to allow for ease of storage within a hospital environment.

SUMMARY

Preferred embodiments of the present invention aim to provide a cost-effective basic means of incubating an infant that can be convenient and easy to store and transport. The present invention also aims to provide a modular arrangement whereby a basic incubator can be supplemented with additional functionality according to the needs and requirements of an infant, an environment or a particular situation.

According to one aspect of the present invention, there is provided a collapsible incubator for an infant, the collapsible incubator comprising:

- a flexible housing for containing the infant, the flexible housing being configurable between an expanded condition and a collapsed condition;
- a door within the flexible housing for infant access;
- a first end portion secured to a first end of the flexible housing;
- a second end portion secured to a second end of the flexible housing, said second end portion being configured to be substantially opposite said first end portion; and,
- at least one fastening means configured to releasably secure the first end portion to the second end portion when in the collapsed condition, whereby the first end portion and the second end portion are configured, in use, to support the flexible housing in the expanded condition, and to substantially contain the flexible housing therebetween in the collapsed condition.

Preferably, the flexible housing incorporates at least one inflatable portion.

Preferably, the inflatable portion comprises a double-walled construction with an air space therebetween, said air space being fluidly connected to at least one air inlet.

The inflatable portion may comprise at least one inflatable rib configured to support the flexible housing in an expanded condition.

Preferably, the inflatable portion is substantially throughout the flexible housing.

The at least one air inlet may incorporate an air flow control means.

The air flow control means may comprise a valve.

Alternatively, or additionally, the air flow control means may comprise a manual air pump.

As a further alternative, the air flow control means may comprise an electric pump.

Yet a further alternative, the air flow control means may comprise a gas canister.

Preferably, the flexible housing incorporates at least one access port for gaining access to the inside of the flexible housing.

The first end portion may incorporate a mounting means for releasably securing a first end module to the first end portion.

The second end portion may incorporate a second mounting means for releasably securing a second end module to the second end portion.

The mounting means and/or second mounting means may comprise at least one mechanical fastener.

The first end module and second end module may be interchangeable.

Preferably, the first end module comprises a heating means.

Preferably, the heating means is fluidly connected to the inside of the flexible housing through the at least one access port within the first end portion.

The flexible housing may incorporate an air distribution means comprising at least one channel and a plurality of holes within said at least one channel.

Preferably, the second end module comprises a cooling means and/or a humidification means.

The second end module may incorporate a storage means.

The collapsible incubator may comprise at least one power means.

The power means may comprise any one or more of the following: mains power, battery power, solar power.

The first end module and/or second end module may comprise a control means operatively connected to the power means for controlling the heating means and/or cooling means and/or humidification means.

The collapsible incubator may comprise at least one sensing means operatively connected to the power means, the at least one sensing means comprising any one or more of the following: heart rate monitor, pulse monitor, infant thermometer, environmental thermometer, thermocouple, motion, blood oxygen level monitor, environmental oxygen level monitor, infant weight, brain activity, a thermostat, moisture level monitor, air quality monitor.

Preferably, the at least one sensor is operatively connected to at least one alert means.

The alert means may be an alarm.

The first end portion and/or the second end portion may incorporate a handle.

Alternatively, the first end module and/or the second end module may incorporate a handle.

The flexible housing comprises at least one transparent portion.

The door may be transparent.

The door may incorporate a sealing means.

Preferably, the fastening means comprises a zip.

Alternatively, the fastening means may comprise any one or more of the following: a mechanical clip, a hook and loop fastener, a strap, a plurality of poppers, a plurality of poppers, an elasticated band or strap The flexible housing may incorporate at least one porthole.

The collapsible incubator may incorporate at least one light-emitting means configured to emit light inside the flexible housing.

Preferably, the flexible housing incorporates means to support the at least one light-emitting means.

The at least one light emitting means may comprise an ultraviolet light source.

The light emitting means may comprise a phototherapy unit.

Alternatively, the light emitting means may comprise an array of light emitting diodes mounted to a flexible strip.

The collapsible incubator may incorporate a water fill port.

The flexible housing may be provided with at least one telescopic rod, configured to support the flexible housing in an expanded condition, the telescopic rod being supported between the first end portion and the second end portion.

The flexible housing may incorporate an oxygen valve.

The flexible housing may comprises a polymer sheet.

Preferably, in use and in an expanded condition, the first end portion and the second end portion are substantially vertical.

Alternatively, in use and in an expanded condition, the first end portion and the second end portion are substantially horizontal.

BRIEF DESCRIPTION OF THE DRAWINGS

For a better understanding of the invention and to show how embodiments of the same may be carried into effect, reference will now be made, by way of example, to the accompanying diagrammatic drawings, in which.

In the figures like references denote like or corresponding parts.

DETAILED DESCRIPTION

Figure 1:
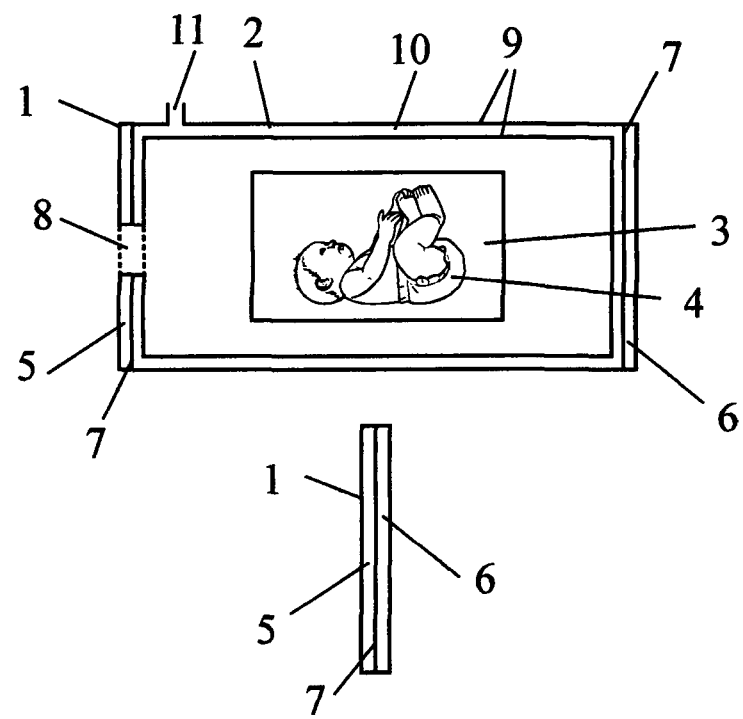
FIG. 1 shows one embodiment of collapsible incubator in side view, in an expanded and collapsed condition.

As shown in FIG. 1, the collapsible incubator 1 comprises a flexible housing 2. This flexible housing 2 is configured to form an enclosure in which an infant 4 that requires incubation of some form can be placed. The flexible housing 2 incorporates a flexible door 3, that allows for the infant 4 to be placed inside and removed from the flexible housing 2, whilst also allowing a user to access the inside of the flexible housing 2 for other purposes. The flexible housing 2 may comprise a tubular or cylindrical form, or may comprise a rectangular or oblong form. The flexible housing 2 may also comprise any other suitable shape where the interior of the flexible housing 2 creates a suitable size of enclosure for incubating an infant 4.

The flexible housing 2 may comprise a single layer of sheet polymer material that is stretched when in an expanded configuration, or when in use as an incubator, and is crumpled when in a collapsed configuration or when stored. The flexible housing 2 may incorporate a number of ribs or structural elements that enable it to maintain a sufficient enclosure when in an expanded configuration, not shown. The flexible housing may alternatively comprise a double-walled construction 9, whereby the double walls 9 leave an air space 10 therebetween. This air space 10 acts as an insulator, helping to maintain a certain temperature within the inside of the flexible housing 2, whilst also providing some structure or rigidity to the flexible housing 2 when in an expanded condition. This double wall arrangement 9 with air space 10 therebetween effectively creates a flexible housing 2 that is an inflatable. The double walls 9 may be throughout the flexible housing 2, or may be in portions of the flexible housing 2. The flexible housing 2 may be double walled 9 in entirety, or the inflatable portions may form structural ribs or portions within the flexible housing 2.

The air space 10 is fluidly connected to an air inlet 11 through which air can be supplied to help to expand the collapsible incubator 1 from a collapsed condition to an expanded condition for use. This air could be blown into the air inlet 11 by the mouth of the user, or alternative means of supplying this air may be included. Such air supplying means may include but is not limited to gas canisters, manual pumps, and electric pumps. The air inlet 11 may incorporate a valve means to prevent air from escaping from the air space 10 during the filling process and whilst in use. The air inlet 11 may simply comprise a stopper to prevent any air from escaping when in use in an expanded condition.

The flexible housing 2 incorporates at least one transparent portion that allows the user to view the infant 4 contained within the flexible housing 2 from outside the flexible housing 2. The door 3 may be transparent. Or the flexible housing 2 may incorporate at least one viewing window. The flexible housing 2 may be transparent in entirety. This allows the user to make visual observations of the infant 4 such as checking skin colour, breathing, and movement, the location of any sensors, feeding tubes or medicinal tubes.

The flexible housing 2 incorporates a pair of end portions 5 and 6, or a first end portion 5 and a second end portion 6. These end portions 5 and 6 are located substantially opposite each other, such that when they are spread apart, they help to open up the flexible housing 2, and provide the flexible housing 2 with some strength and structure when in an expanded form. The first end portion 5 and the second end portion 6 may be substantially the same size, and may comprise planar portions, of rigid polymer, or otherwise, and be configured to be at opposite ends of the flexible housing 2. The first end portion 5 and the second end portion 6 are configured such that in a collapsed condition the can contain the flexible housing 2 when in a collapsed form. These end portions 5 and 6 may comprise shallow shells into which the collapsed flexible housing 2 can be folded or compressed.

The end portions 5 and 6 may not be substantially opposite each other in all embodiments, but are configured such that be bringing the first end portion 5 into contact with the second end portion 6 the flexible housing 2 is collapsed therebetween.

The first end portion 5 and/or the second end portion 6 may incorporate one or more access points 8. These access points 8 may also be formed within the flexible housing 2. The access points within the end portions 5 and 6 and the access points within the flexible housing 2 may correspond with each other to allow entry through either the first end portion 5 or the second end portion 6, and through the flexible housing 2, to the interior of the flexible housing 2.

Where the flexible housing 2 comprises a double wall arrangement 9, the access port 8 would be suitable sealed by welding or otherwise, so as not to allow air from the air space 10 to escape through this access port 8. These access ports 8 allow for the entry of cables, sensors, wires, heated air, cooled air, moisture and other components and elements that support the incubation process of the infant 4 being incubated within the flexible housing 2.

The first end portion 5 is provided with a fastening means 7 and the second end portion 6 is providing with a corresponding fastening means 7 that allow the first end portion 5 to be releasably secured to the second end portion 6 when in a collapsed or stored condition. This is to allow the collapsible incubator 1 to be easily transported in a collapsed condition. It also means that the flexible housing 2 which is likely to have been sterilised prior to use, is kept free from the ingress of dirt and other detritus before the collapsible incubator 1 is expanded for use. FIG. 1 shows the collapsed condition, beneath the expanded condition, where the flexible housing 2 cannot be seen as it is substantially contained within or between the first end portion 5 and the second end portion 6.

Figure 2A:
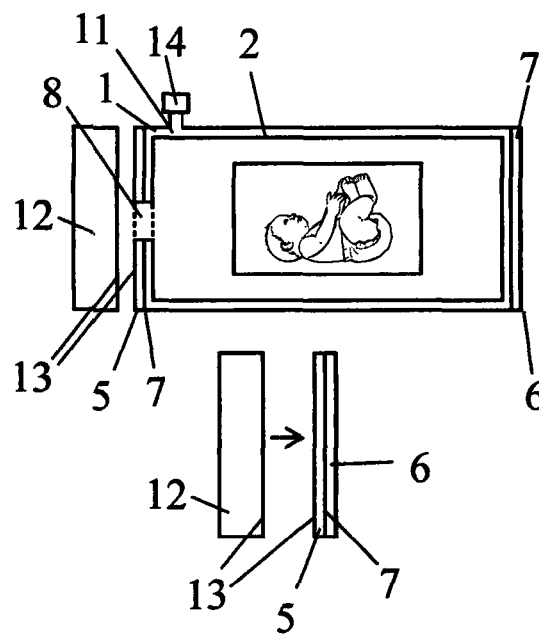
FIG. 2A shows the collapsible incubator of FIG. 1 in expanded and collapsed condition, showing one embodiment of first end module prior to mounting to a first end portion.
Figure 2B:
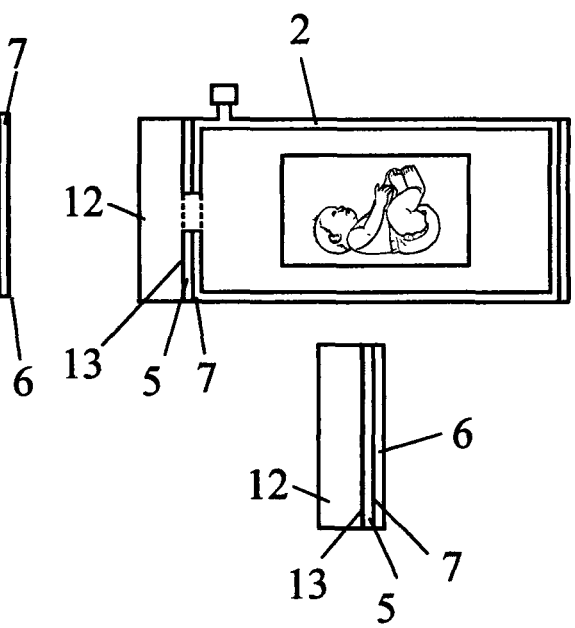
FIG. 2B shows the collapsible incubator of FIG. 2A in an expanded and collapsed condition, showing the first end module mounted to the first end portion.

FIGS. 2A and 2B show the collapsible incubator 1 of FIG. 1 with one embodiment of a first end module 12 releasably mounted by a mounting means 13 to the first end portion 5. This first end module 12 may comprise any number of functions that are required by the collapsible incubator 1 when incubating an infant 4. This first end module 12 may be operatively connected to the access port 8 to allow for the functions of the first end module 12 to be conveyed to the infant 4 through the access port 8.

The mounting means 13 for mounting the first end module 12 to the first end portion 5 may comprise any suitable mechanical mounting means such as clips or clamps, or may alternatively comprise other suitable mounting means 13 such as hook and loop fasteners. The first end module 12 can be added to the collapsible incubator 1 as and when required and specific for a certain use. This modular arrangement of end modules allows for different combinations of end modules to be added to the basic collapsible incubator 1, according to requirements or to meet various budget constraints.

The air inlet 11 is shown here with a pump 14, to provide air either manually or electrically to the air space 10 between walls 9. The pump 14 and air inlet 11 in a collapsed condition would fold within the boundaries of the first end portion 5 and the second end portion 6 to be substantially contained therebetween.

Figure 3:
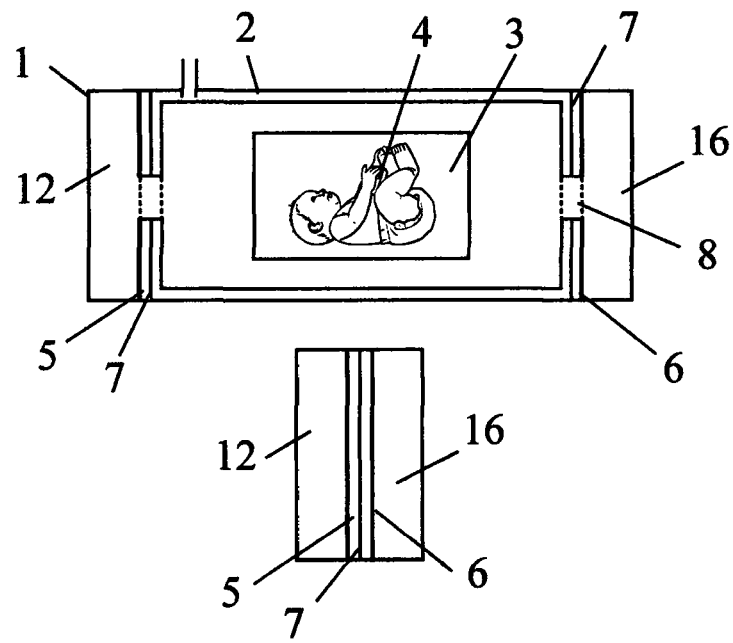
FIG. 3 shows the collapsible incubator of FIG. 2B in an expanded and collapsed condition, showing a second end module mounted to a second end portion.

FIG. 2A shows the first end module 12 detached from the collapsible incubator 1, in both an expanded and a collapsed condition. FIG. 2B shows the same collapsible incubator 1 with the first end module 12 attached to the first end portion 5, in both an expanded and collapsed condition. FIG. 3 shows a further end portion, or second end portion 16, that is provided with mounting means 13 for releasably mounting the second end module 16 to the second end portion 6. In an alternative embodiment, the first end portion 5 is formed as part of the first end module 12 and the second end portion 6 is formed as part of the second end portion 6, and the end modules 12 and 16 are therefore permanently part of the flexible housing 2.

FIG. 3 shows the collapsible incubator 1 with first end module 12 and second end module 16 mounted to either end portion 5 and 6, in both an expanded and a collapsed condition.

Figure 4:
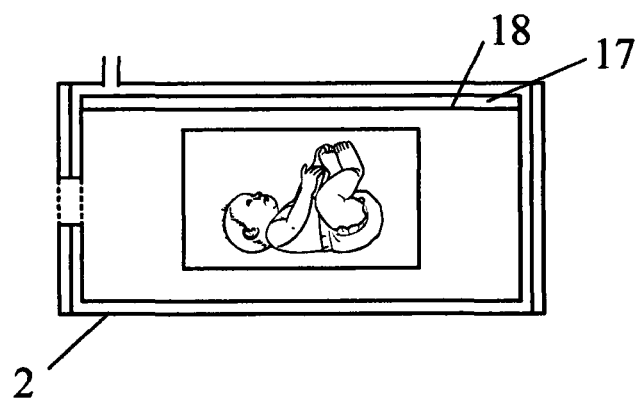
FIG. 4 shows the collapsible incubator of FIG. 1 in an expanded condition, showing one embodiment of light emitting means supported within the flexible housing.

FIG. 4 shows one embodiment of support means 18 for a light emitting means 17. The light emitting means 17 is configured to provide light to the infant 4 contained within the flexible housing 2. This light may comprise a plurality of light-emitting diodes, or may comprise one or more ultraviolet light sources, for therapeutic and visibility purposes. The flexible housing 2 may incorporate one or more elements to support these light emitting means 17 within the flexible housing 2.

Figure 5:
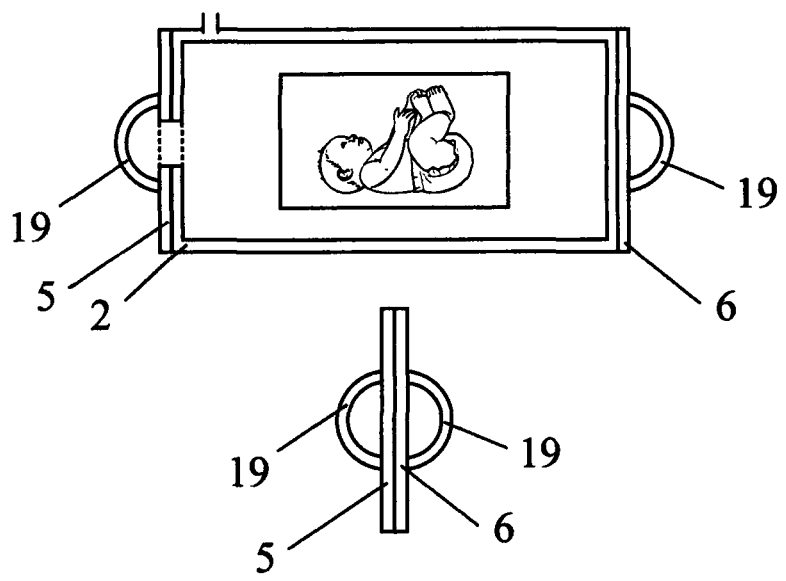
FIG. 5 shows the collapsible incubator of FIG. 1 of FIG. 1 in an expanded and collapsed condition, showing one embodiment of handles within the first end portion and the second end portion.
Figure 6A:
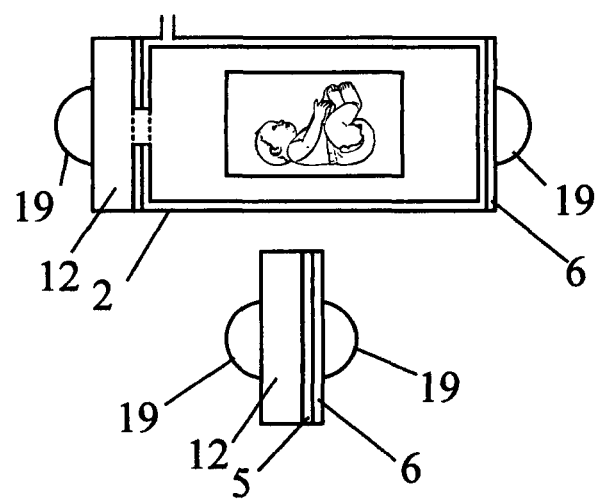
FIGS. 6A and 6B show the collapsible incubator in an expanded and collapsed condition, with a combination of first and second end modules, showing different possible configurations of handles within the first and second end portions and/or first and second end modules.
Figure 6B:
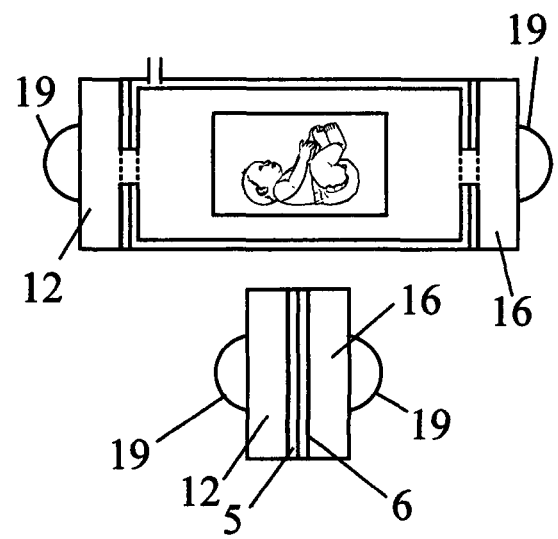

FIG. 5 shows one arrangement of handle means 19 providing on the first end portion 5 and the second end portion 6 and configured to help the user to expand, collapse and carry the collapsible incubator 1. FIG. 6A shows the handles 19 when the first end module 12 is attached, and FIG. 6B shows the handles 19 when both end modules 12 and 16 are attached. The end portions 5 and 6 may be provided with handles 19 even if the end modules 12 and 16 are attached, although these would be concealed in this case and not used. Again FIGS. 6A and 6B show the various configurations of handle in both a collapsed and an expanded condition.

Figure 7:
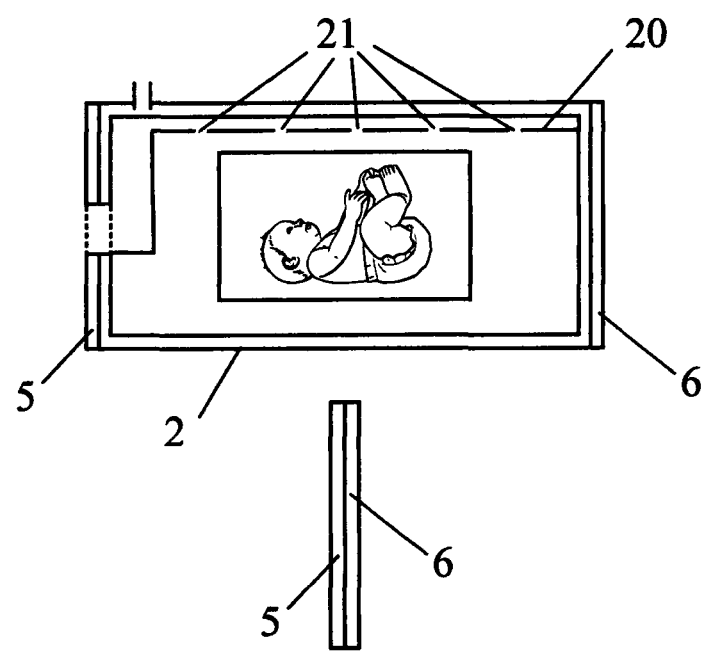
FIG. 7 shows the collapsible incubator of FIG. 1, showing one embodiment of air distribution means incorporating a plurality of holes.

FIG. 7 shows one embodiment of internal air distribution means 20 comprising at least one air channel 20 and a plurality of holes 21 to supply air from the air channels to the interior cavity of the flexible body 2. The air channel 20 may be in fluid communication with either the first end portion 5 or the second end portion 6, and therefore the first end module 12 or the second end module 16. This is to enable air to be supplied directly to the infant 4. Such air may have been heated or cooled, or may have be supplemented in some way to help support the life of the infant 4.

Figure 8:
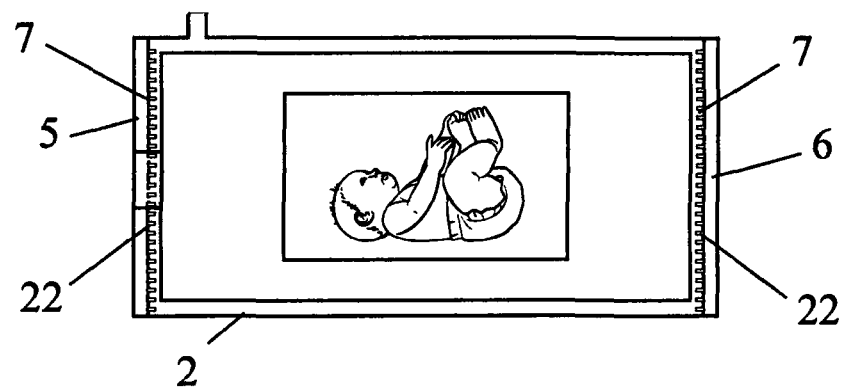
FIG. 8 shows the collapsible incubator of FIG. 1, showing one embodiment of fastening means comprising a zip.

FIG. 8 shows one embodiment of fastening means 7 shown as a zip or zipper 22. This zip 22 incorporates one portion of teeth on the first end portion 5 and the corresponding portion of teeth on the second end portion 6, and a zip 22 to zip the first end portion 5 to the second end portion 6, containing the flexible body 2 in a collapsed condition therebetween. Alternative fastening means may comprise hook and loop fasteners, poppers, mechanical clips, straps or other fastening means 7 suitable for securing together the first end portion 5 to the second end portion 6 and to containing the flexible housing 2 in between.

Figure 9:
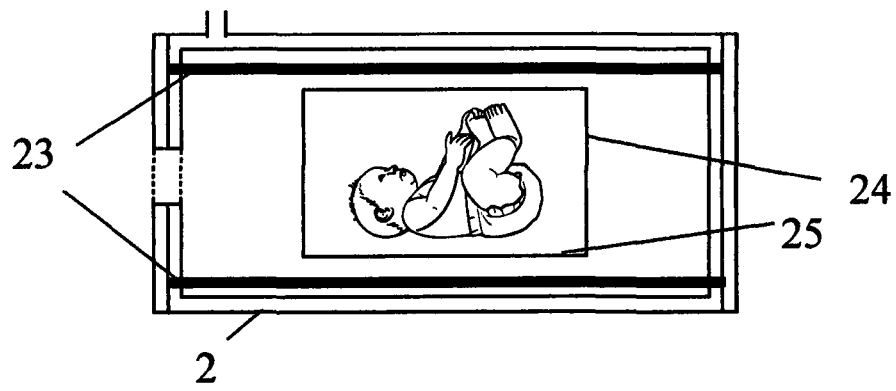
FIG. 9 shows the collapsible incubator of FIG. 1, showing one embodiment of flexible housing support means.

As shown in FIG. 9, the flexible housing 2 may be provided with additional means of support 23 that in this embodiment comprise telescopic rods 23. These rods stretch between the first end portion 5 and the second end portion 6 and help to keep the flexible housing 2 in an open and expanded condition. These rods 23 are telescopic so that they too can collapse to be contained within the collapsible incubator 1 when in a collapsed condition. The flexible door 3 may be joined to the flexible body 2 by a hinge 25, or may form a removable piece. It may incorporate sealing means about the periphery 24 to prevent the ingress of dirt, detritus and suchlike and to help maintain a sterile incubated environment with the flexible housing 2. The door 3 may be closed by a zip, not shown.

Figure 10:
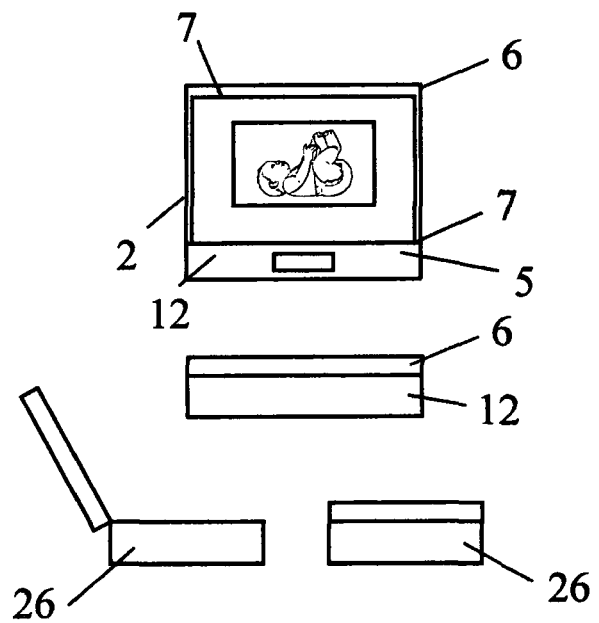
FIG. 10 shows a further embodiment of collapsible incubator, shown in an expanded and collapsed condition, the first end portion and second end portion being configured, in use, to be substantially horizontal, and also showing a carrying case.

FIG. 10 shows a further embodiment of collapsible incubator 1 where the first end portion 5 and the second end portion 6 are shown in a vertical configuration, where one is substantially above the other. This arrangement of collapsible incubator 1 therefore expands and collapses in along a vertical plane. The collapsible incubator 1 may be contained within a carrying case 26 for transporting from place to place, and the carrying case 26 may form part of the first or second end modules 12 or 16.

Figure 11:
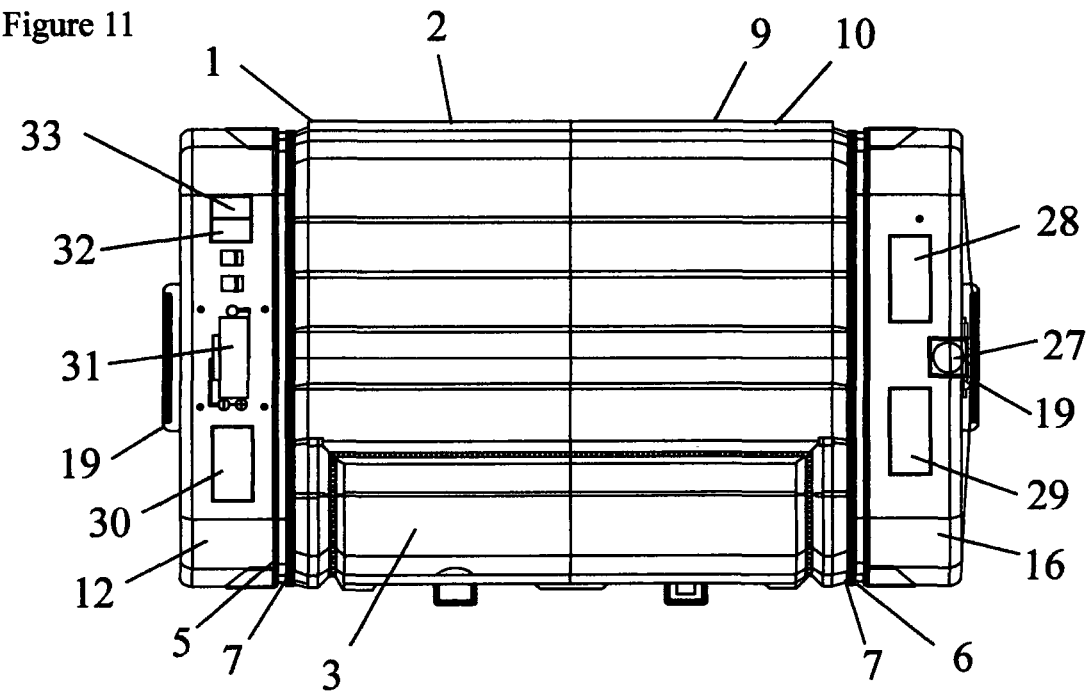
FIG. 11 shows a detailed plan view of the collapsible incubator of FIG. 6B shown in an expanded condition.

FIG. 11 shows the collapsible incubator 1 in some detail and in plan view. The first end module 12 is provided with at least one heating means 30 that may comprise heated wires, ceramic heaters, or other form of heat to warm the surrounding air. The heating means 30 or first end module 12 may be provided with a fan to drive the heated air 15 through an access port 8 within the first end portion 5 and the flexible body 2 and into the interior of the flexible body 2. This heated air may also be passed through the air distribution means 20 as aforementioned. The first end module 12 may also incorporate at least one control means 31 for controlling the collapsible incubator 1, and its various functions. The control means 31 may be operatively connected to any elements that require controlling within the collapsible incubator 1.

The control means 31 may be operatively connected to one or more sensors 32 for sensing various vital signs of the infant 4. Such vital signs might include but are not limited to heart rate, pulse, temperature, blood oxygen concentration, breathing, humidity. Environmental condition monitoring may also be included to track the temperature of the environmental within the flexible housing 2, and the humidity of this environment. These sensors 32 may therefore include one or more of the following: infant thermometer, environmental or ambient thermometer, thermocouple, heart rate monitor, pulse monitor, ventilator, cardio-respiratory monitor, intravenous therapy pump, pulse oximeter, oxygen sensor, weight scales, brain activity monitor, thermostat and an oxygen supply means sensor. The sensors 32 are configured within the flexible body 2 and operatively connected to the control means 31 and at least one power means 33 through the access port 8. The control means 31 may comprise an alert means such as an alarm, to alert a user when a reading from a sensor 32 is of a certain value that is to be of concern.

The second end module 16 may be configured to provide cooling means 28 and/or humidification means 29 to the interior of the flexible housing 2. For this purpose the second end module 16 may be provided with a water inlet 27 that is in fluid communication with the cooling means 28 and the humidification means 29.

Figure 12:
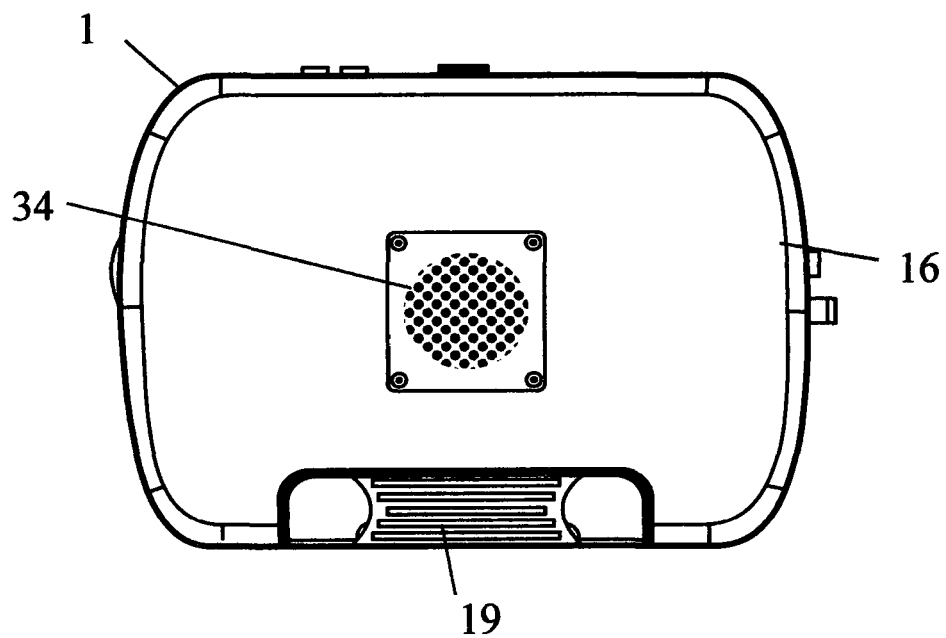
FIG. 12 shows the collapsible incubator of FIG. 11 in end view.

FIG. 12 shows a grill cover 34 for preventing the ingress of dirt and detritus to the workings of the second end portion 16, through any air inlets. It also shows an alternative embodiment of handle 19.

Figure 13:
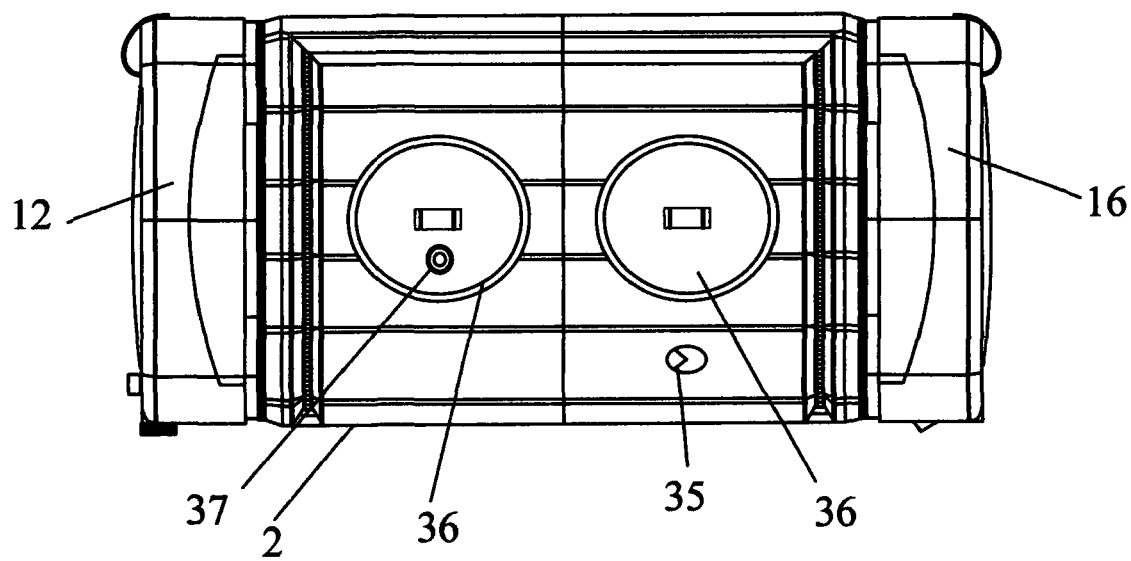
FIG. 13 shows the collapsible incubator of FIG. 11 in front view.

FIG. 13 shows a front view of the collapsible incubator 1 showing a pair of portholes 36 within the door 3 to gain access to the infant 4 without the need to open and close the door 3. These portholes may alternatively be within the flexible housing 2. One of these portholes 36 is shown provided with an access port 8 or oxygen valve 37 for providing a supply of oxygen to the infant 4. The oxygen supply may be to the environment within the flexible housing 2, or may be direct to the infant 4 through a tube and mask. Also shown in this figure is an access port 8 for a feeding tube 35 for supplying liquid food substances to an infant 4 through a tube or line, either intravenously or otherwise.

Figure 14:
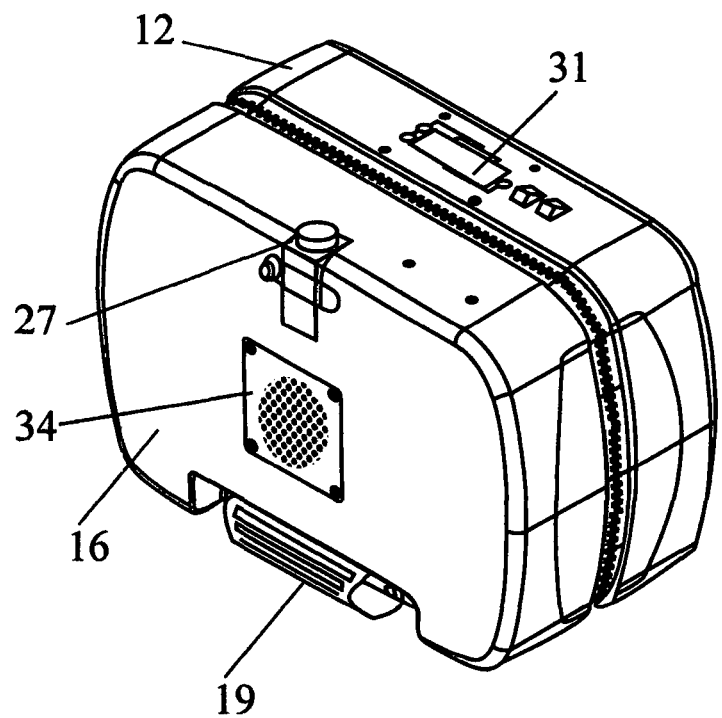
FIG. 14 shows the collapsible incubator of FIG. 11 in isometric view when in a collapsed condition.

FIG. 14 shows the collapsible housing 2 contained within the first end module 12 and the second end module 16, with the first end portion 5 secured by zipper 22 to the second end portion 6. In its collapsed form the collapsible incubator I is through to be convenient to transport, ship, stack and carry.

The collapsible incubator 1 may be provided as a disposable unit, for single use with one infant 4, and be made of suitable materials to allow for ease of recycling, disposal or incineration.

Alternatively, the collapsible incubator 1 may be provided as a reusable unit that can be reused with the same or another infant 4. In this instance the collapsible incubator 1 must be easy to clean and sterilise, and be configured to go through a sterilisation process. In particular the flexible housing 2 should be easy to sterilise, and any creases or joins should be minimised to prevent build-up of dirt or bacteria.

The invention claimed is:

1. A collapsible incubator for an infant, the collapsible incubator comprising:
    a flexible housing for containing the infant, the flexible housing being configurable between an expanded condition and a collapsed condition;
    a door within the flexible housing for infant access;
    a first end portion secured to a first exterior portion of the flexible housing;
    a second end portion secured to a second exterior portion of the flexible housing;
    a carrying case; and
    at least one fastening means configured to releasably secure the first end portion to the second end portion when in the collapsed condition, whereby the first end portion and the second end portion are configured, in use, to support at least a portion of the flexible housing in the expanded condition, and to substantially contain the flexible housing therebetween in the collapsed condition; wherein
    the first end portion incorporates a mounting means for releasably securing a first end module to the exterior of the first end portion; wherein
    the flexible housing incorporates at least one inflatable portion; and
    the carrying case has a base portion comprising at least part of the first end module and a lid portion connected via a hinge to the base portion; and wherein the first end module operably forms a bottom side of the incubator in the expanded configuration, and the flexible housing operably extends vertically from the first end module.

2. A collapsible incubator according to claim 1, wherein the inflatable portion comprises a double-walled construction with an air space therebetween, said air space being fluidly connected to at least one air inlet.

3. A collapsible incubator according to claim 2, wherein the inflatable portion comprises at least one inflatable rib configured to support the flexible housing in an expanded condition.

4. A collapsible incubator according to claim 2, wherein the at least one air inlet incorporates an air flow control means.

5. A collapsible incubator according to claim 1, wherein the flexible housing incorporates at least one access port for gaining access to the inside of the flexible housing.

6. A collapsible incubator according to claim 1, wherein the second end portion incorporates a second mounting means for releasably securing a second end module to the second end portion.

7. A collapsible incubator according to claim 6, wherein the collapsible incubator comprises at least one power means.

8. A collapsible incubator according to claim 1, wherein the first end module comprises a heating means.

9. A collapsible incubator according to claim 8, wherein the heating means is fluidly connected to the inside of the flexible housing through an access port within the first end portion.

10. A collapsible incubator according to claim 9, wherein the flexible housing incorporates an air distribution means comprising at least one channel and a plurality of holes within said at least one channel.

11. A collapsible incubator according to claim 1, comprising at least one sensing means, wherein the at least one sensing means is operatively connected to at least one alert means.

12. A collapsible incubator according to claim 1, wherein the flexible housing comprises at least one transparent portion.

13. A collapsible incubator according to claim 1, wherein the flexible housing incorporates at least one porthole.

14. A collapsible incubator according to claim 1, wherein the collapsible incubator incorporates at least one light-emitting means configured to emit light inside the flexible housing.

15. A collapsible incubator according to claim 1, wherein the collapsible incubator incorporates a water fill port.

16. A collapsible incubator according to claim 1, wherein the flexible housing is provided with at least one telescopic rod, configured to support the flexible housing in an expanded condition, the telescopic rod being supported between the first end portion and the second end portion.

17. A collapsible incubator according to claim 1, wherein the flexible housing incorporates an oxygen valve.

* * * * *